United States Patent [19]
Yamamoto et al.

[11] Patent Number: 5,399,571
[45] Date of Patent: Mar. 21, 1995

[54] NEUROPROTECTIVE DRUG

[75] Inventors: Noriko Yamamoto, Moriguchi; Koichi Yokota, Sakai; Akira Yamashita, Nishinomiya; Keizo Ito, Osaka, all of Japan

[73] Assignee: Kanebo, Ltd., Tokyo, Japan

[21] Appl. No.: 16,860

[22] Filed: Feb. 12, 1993

[30] Foreign Application Priority Data

Feb. 25, 1992 [JP] Japan .................................. 4-075256

[51] Int. Cl.⁶ ........................................... A61K 31/425
[52] U.S. Cl. .................................................... 514/365
[58] Field of Search ................................. 514/365, 822

[56] References Cited

U.S. PATENT DOCUMENTS 4,168,315 9/1979 Rynbrandt et al. .................. 514/365
4,659,726 4/1987 Yoshino et al. ..................... 514/365

FOREIGN PATENT DOCUMENTS 0159677 10/1985 European Pat. Off. .

OTHER PUBLICATIONS

Seminars in Neurology, vol. 11, No. 4, Dec. 1991, pp. 353–367, J. Biller et al. 'Antithrombotic therapy for ischemic cerebrovascular disease'.
Dialog Information Services, File 55, Accession No. 9325804 & JPN J Pharmacol (Suppl. 1), vol. 59, 1992, p. 346P, N. Yamamoto et al., 'Protective effect of KBT-3022 a new anti-platelet agent in experimental cerebral ischemic models'.

Primary Examiner—Raymond Henley, III
Assistant Examiner—K. Weddington
Attorney, Agent, or Firm—Foley & Lardner

[57] ABSTRACT

A neuroprotecting drug comprises as an essential active ingredient ethyl 2-[4,5-bis(4-methoxyphenyl)thiazol-2-yl]pyrrol-1-yl acetate, which is useful with high safety for the prophylaxis and treatment of brain dysfunction induced by hypoxia due to the disturbance of cerebral circulation such as cerebral hemorrhage or cerebral infarction in human being.

2 Claims, No Drawings

NEUROPROTECTIVE DRUG

This invention relates to a novel neuroprotective drug, more particularly to a neuroprotective drug containing as an essential active ingredient ethyl 2-[4,5-bis(4-methoxyphenyl)thiazol-2-yl]pyrrol-1-yl acetate [hereinafter, it is abbreviated as "KBT-3022"] which is represented by the following formula:

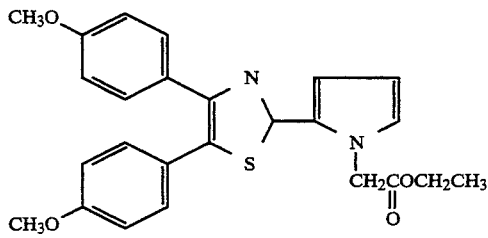

PRIOR ART

The brain is an organ which has an extremely high metabolic activity, but the brain significantly loses its function in the state of hypoxia induced by disturbance of cerebral circulation such as cerebral hemorrhage and cerebral infarction. Even if the circulation of blood within the brain is restored after such a cerebral circulation disturbance, the lipids within the cerebral cells are peroxidized by active oxygen, and hence, there is still a problem of cerebral cell disturbance due to the lipid peroxides.

U.S. Pat. No. 4,659,726 discloses some specific diphenylpyrrolylthiazole derivatives which include the specific compound KBT-3022 used in the present invention and processes for the preparation of said compounds, and further discloses that these compounds are useful as a platelet aggregation inhibitor. However, this U.S. patent does not mention any neuroprotective activity of the KBT-3022 compound.

OBJECT OF THE INVENTION

The present inventors have extensively studied to develop a new neuroprotective drug having excellent protective activity against brain dysfunction induced by hypoxia due to the disturbance of cerebral circulation such as cerebral hemorrhage or cerebral infarction, and having high safety with low toxicity suitable for the clinical use thereof, and have found that the specific compound KBT-3022 has potent neuroprotective activity satisfying the above requirements.

Thus, an object of the invention is to provide a novel neuroprotective drug. Another object of the invention is to provide a pharmaceutical composition useful as a neuroprotective drug comprising as an essential active ingredient KBT-3022 in admixture with a conventional pharmaceutically acceptable carrier or diluent. A further object of the invention is to provide a method for the prophylaxis and treatment of brain dysfunction induced by hypoxia due to the disturbance of cerebral circulation such as cerebral hemorrhage or cerebral infarction by the oral administration of KBT-3022. Still a further object of the invention is the use of KBT-3022 as a neuroprotecting drug. These and other objects and advantages of the invention will be apparent to those skilled in the art from the following description.

DETAILED DESCRIPTION OF THE INVENTION

The neuroprotective drug of the invention is usually in the form of a pharmaceutical composition comprising as an essential active ingredient the abovementioned specific compound KBT-3022 in admixture with a conventional pharmaceutically acceptable carrier or diluent, which is prepared by a conventional method.

The pharmaceutical composition of the invention is preferably formulated in the form of a preparation suitable for oral administration, for example, solid preparations such as tablets, granules, powders, capsules, etc., and liquid preparations such as syrups. The pharmaceutical composition can be prepared by a conventional method. For instance, the solid preparations are usually prepared by using a conventional pharmaceutically acceptable carrier, such as lactose, corn starch, crystalline cellulose, carboxymethylcellulose calcium, carboxymethylcellulose, talc, magnesium stearate, etc. The capsules can be prepared by encapsulating the granules, powders, etc. to form suitable capsules. The syrups can be prepared by dissolving or suspending KBT-3022 in an aqueous solution containing white sugar, carboxymethylcellulose, etc. The pharmaceutical composition usually contains the KBT-3022 as an essential active ingredient in an amount of 1 mg to 20 mg in a dosage unit.

The neuroprotective drug of the invention is usually administered orally for the purpose of the prophylaxis or treatment of brain dysfunction induced by hypoxia due to the disturbance of cerebral circulation such as cerebral hemorrhage or cerebral infarction. The dose of the neuroprotective drug of the invention may vary depending upon the severity of the diseases, weight and age of the patients and the like, but is usually in the range of 2 to 100 mg per day in adults, which may be administered in a single dose or 2 to 3 divided doses.

The KBT-3022 has excellent protecting properties against brain dysfunction induced by various hypoxic injuries as shown in Tests 1 to 3, with extremely low toxicity as shown in Test 4. KBT-3022 inhibited significantly the production of undesirable lipid peroxides induced by auto-oxidation of cerebral homogenate of a guinea pig. Thus, the drug of the invention containing the KBT-3022 as an essential active ingredient is suitable for clinical use as a neuroprotecting drug in human beings.

TEST 1

Effect on survival time of mice subjected to normobaric hypoxia:
(1) Test compound:
(i) KBT-3022
(ii) Pentobarbital sodium (as a reference compound)
(2) Test method:

The test compound was administered orally to ddY male mice (weighing 18-24 g) fasted overnight in the form of a solution or suspension in 0.5% polyoxyethylene sorbitan monooleate (=0.5% Tween 80).

A transparent plastic box (volume: 27 liters) with an exhaust vent was purged with nitrogen gas by passing through 100% nitrogen gas at a rate of 10 liter/minute to provide a low oxygen atmosphere (oxygen concentration within the box: <0.5%). The mice, one hour after the administration of the test compound as above, were put in the box, and the survival time (sec) of mice after being put in the box was measured. In the control group, the mice were administered only the solvent (0.5% Tween 80), and the survival time of the mice was measured likewise.

(3) Test results:

The test results are shown in Table 1. As is clear from the test results, KBT-3022 showed prolongation of the survival time of mice subjected to normobaric hypoxia.

TABLE 1

| Test compound | Dose (mg/kg) | Number of mice | Survival time (sec) average ± S.E. |
|---|---|---|---|
| KBT-3022 | 1 | 5 | 23.9 ± 0.6 |
| | 3 | 5 | 25.6 ± 1.0* |
| | 10 | 5 | 26.2 ± 1.0** |
| Pentobarbital | 10 | 5 | 22.1 ± 0.5 |
| sodium | 30 | 5 | 32.1 ± 1.5** |
| Control group | — | 10 | 22.5 ± 0.2 |

*Significant difference to the control group, p < 0.05
**Significant difference to the control group, p < 0.01 (by Dunnett's test)

TEST 2

Protective effects on the KCN-induced hypoxia which caused death in mice:

(1) Test compound:
(i) KBT-3022
(ii) Pentobarbital sodium (as a reference compound)

(2) Test method:

The test compound was administered orally to ddY male mice (weighing 18–24 g) fasted overnight in the form of a solution or suspension in 0.5% polyoxyethylene sorbitan monooleate (=0.5% Tween 80). One hour after the administration of the test compound, the mice were further rapidly administered a KCN-physiological saline solution (3 mg/kg) into the tail vein, and after 30 minutes the survival number of mice was measured. In the control group, the mice were administered only the solvent (0.5% Tween 80), and the survival number of mice was measured likewise.

(3) Test results:

The test results (survival number of mice/number of test mice) are shown in Table 2. As is clear from the test results, KBT-3022 showed significant protective effects on the KCN-induced hypoxia which caused death in mice.

TABLE 2

| Dose (mg/kg) | Test compound | |
|---|---|---|
| | KBT-3022 | Pentobarbital Na |
| 1 | 2/10 | — |
| 3 | 4/10* | — |
| 10 | 4/10* | 1/10 |
| 30 | 5/10* | 9/10*** |
| 100 | 5/10* | — |

*Significant difference to the control group (0/10), p < 0.05
***Significant difference to the control group (0/10), p < 0.001 (by Fisher's exact probability test)

TEST 3

Effect on ischemia-induced brain edema:
(1) Test compound:
KBT-3022
(2) Test method:
Gerbils (weighing 61–78 g) fasted overnight were orally administered the test compound in the form of a suspension in 0.5% polyoxyethylene sorbitan monooleate (=0.5% Tween 80). Three hours after the administration of the test compound, the gerbils were operated to expose the common carotid arteries of both sides, and the common carotid arteries were ligated with an aneurysm clip. Fifteen minutes after ligation, the clip was removed to allow reperfusion. Four hours after the reperfusion, the head of each gerbil was cut and the brain was taken out. The weight (in wet) of the brain thus taken out was measured, and thereafter, the brain was dried at 90° C. overnight and the weight (in dry) of the brain was measured. The water content of the brains was calculated by the following equation:

$$\text{Water content (\% by weight)} = \frac{\left(\begin{array}{c}\text{Weight}\\\text{in wet}\end{array}\right) - \left(\begin{array}{c}\text{Weight}\\\text{in dry}\end{array}\right)}{\text{Weight in wet}} \times 100$$

In the control group, the gerbils were administered only the solvent (0.5% Tween 80), and the water content was measured likewise. In the non-treated group, the gerbils were administered only the solvent (0.5% Tween 80), and after the operation, the brain was taken out without subjecting to the ligation treatment, and then the water content of the brain was measured likewise.

(3) Test results:

The test results are shown in Table 3. As is clear from the test results, KBT-3022 inhibited significantly the brain edema (increase of water content in the brain) induced by transient forebrain ischemia in gerbils.

TABLE 3

| Test compound | Dose (mg/kg) | Number of mice | Water content (%) average ± S.E. |
|---|---|---|---|
| KBT-3022 | 1 | 6 | 79.5 ± 0.1 |
| | 3 | 6 | 79.3 ± 0.1** |
| | 10 | 6 | 79.2 ± 0.1** |
| Control group | — | 6 | 79.7 ± 0.1 |
| Non-treated group | — | 6 | 78.9 ± 0.1** |

**Significant difference to the control group, p < 0.01 (by Dunnett's test)

TEST 4

Acute toxicity:
(1) Test compound:
KBT-3022
(2) Test method:

The test compound was administered orally to ddY male mice (weighing 18–23 g, 5 mice per group) fasted overnight in the form of a suspension in 1% gum arabic solution and it was observed whether the mice would die or not for 10 days.

(3) Test results:

No mice died by administration of KBT-3022 even at a dose of 5000 mg/kg. Thus, KBT-3022 has a $LD_{50}$ of >5000 mg/kg by oral administration.

When the same acute toxicity test STET also done in rats and dogs, the same results as the above were obtained. KBT-3022 showed also a very low toxicity in the sub-acute toxicity test in mice, rats and dogs and further in the chronic toxicity test in mice and dogs.

The pharmaceutical composition of this invention is illustrated by the following Examples.

EXAMPLE 1

Preparation of Tablets:

[Formulation]

| Components | Amount (g) |
| --- | --- |
| KBT-3022 | 40 |
| Lactose | 1600 |
| Crystalline cellulose | 1580 |
| Carboxymethylcellulose calcium | 100 |
| Carboxymethylcellulose | 60 |
| Magnesium stearate | 20 |
| Totally | 3400 |

[Procedure]

The above components are uniformly mixed, and the mixture is tabletted by a conventional method to give tablets (170 mg per tablet).

EXAMPLE 2

Preparation of Tablets:

[Formulation]

| Components | Amount (g) |
| --- | --- |
| KBT-3022 | 100 |
| Lactose | 1560 |
| Crystalline cellulose | 1560 |
| Carboxymethylcellulose calcium | 120 |
| Talc | 40 |
| Magnesium stearate | 20 |
| Totally | 3400 |

[Procedure ]

The above components are uniformly mixed, and the mixture is tabletted by a conventional method to give tablets (170 mg per tablet).

EXAMPLE 3

Preparation of Powders:

[Formulation]

| Components | Amount (g) |
| --- | --- |
| KBT-3022 | 5 |
| Lactose | 585 |
| Corn starch | 410 |
| Totally | 1000 |

[Procedure ]

The above components are uniformly mixed, and the mixed powder is packed to give packed powders (1 g per pack).

What is claimed is:

1. A method for the treatment of brain dysfunction induced by hypoxia due to the disturbance of cerebral circulation, which comprises administering orally about 2 to 100 mg per day of ethyl 2-[4,5-bis(4-methoxyphenyl)thiazol-2-yl]pyrrol-1-yl acetate to a patient suffering from the disturbance of cerebral circulation.

2. A method for the treatment of brain dysfunction induced by hypoxia due to cerebral hemorrhage or cerebral infarction, which comprises administering orally about 2 to 100 mg per day of ethyl 2-[4,5-bis(4-methoxyphenyl)thiazol-2-yl]pyrrol-1-yl acetate to a patient suffering from the cerebral hemorrhage or cerebral infarction.

* * * * *